(12) United States Patent
Chen

(10) Patent No.: US 9,285,334 B2
(45) Date of Patent: Mar. 15, 2016

(54) HYBRID DIELECTRIC MOISTURE SENSORS

(71) Applicant: Zhi David Chen, Lexington, KY (US)

(72) Inventor: Zhi David Chen, Lexington, KY (US)

( * ) Notice: Subject to any disclaimer, the term of this patent is extended or adjusted under 35 U.S.C. 154(b) by 237 days.

(21) Appl. No.: 13/911,371

(22) Filed: Jun. 6, 2013

(65) Prior Publication Data

US 2014/0361794 A1 Dec. 11, 2014

(51) Int. Cl.
*G01R 27/26* (2006.01)
*G01N 27/22* (2006.01)

(52) U.S. Cl.
CPC ............ *G01N 27/223* (2013.01); *G01N 27/226* (2013.01)

(58) Field of Classification Search
CPC .. G01N 27/223; G01N 27/226; G01N 27/225
See application file for complete search history.

(56) References Cited

U.S. PATENT DOCUMENTS

| | | | |
|---|---|---|---|
| 4,143,177 A | 3/1979 | Kovac et al. | |
| 4,203,087 A | 5/1980 | Chleck et al. | |
| 5,050,434 A * | 9/1991 | Demisch | G01N 27/225 361/286 |
| 5,571,944 A * | 11/1996 | Pfeifer | G01N 29/022 310/313 R |
| 6,445,565 B1 * | 9/2002 | Toyoda | G01N 27/225 257/301 |
| 7,181,966 B2 * | 2/2007 | Isogai | G01N 27/223 326/105 |
| 7,871,891 B2 * | 1/2011 | Cho | H01L 27/0207 257/301 |
| 8,821,794 B2 * | 9/2014 | Gridelet | G01N 33/5438 422/82.01 |
| 2004/0149032 A1 * | 8/2004 | Sell | G01F 23/268 73/304 C |
| 2008/0251929 A1 * | 10/2008 | Kageyama | H01L 21/76816 257/773 |
| 2008/0316673 A1 * | 12/2008 | Hoofman | G01N 27/223 361/286 |
| 2011/0179861 A1 * | 7/2011 | Grange | B82Y 15/00 73/335.04 |
| 2011/0223766 A1 * | 9/2011 | Kobayashi | H01L 21/02126 438/694 |

FOREIGN PATENT DOCUMENTS

CN    1023155 C    12/1993

OTHER PUBLICATIONS

Z. Chen, M.-C. Jin, C. Zhen, and G. Chen, "Properties of Modified Anodic-Spark-Deposited Alumina Porous Ceramic Films as Humidity Sensors," J. Am. Ceram. Soc. 74,1325 (1991).
Z. Chen and M.-C. Jin, "An Alpha-Alumina Moisture Sensor for Relative and Absolute Humidity Measurement," in Proc. 27th Annual Conf. IEEE Industry Appl. Soc., IEEE Industry Appl. Soc., Houston, TX, 1992, vol. 2, p. 1668.
Z. Chen and C. Lu, "Humidity Sensors: A Review of Materials and Mechanisms," Sensor Letters 3, 274-295 (2005).

* cited by examiner

*Primary Examiner* — Tung X Nguyen
*Assistant Examiner* — Dominic Hawkins
(74) *Attorney, Agent, or Firm* — King & Schickli, PLLC

(57) ABSTRACT

A moisture sensor includes a first electrode, a layer of porous insulating material including a plurality of pores, a film of dielectric sensing material covering the inner surfaces of the plurality of pores and a second electrode.

20 Claims, 3 Drawing Sheets

HYBRID DIELECTRIC MOISTURE SENSORS

This invention was made with government support under contract KSEF-148-502-12-300 awarded by Kentucky Science and Engineering Foundation. The government has certain rights in the invention.

TECHNICAL FIELD

This document relates generally to the field of electronic sensors and, more particularly, to a new and improved moisture sensor and method for making the same.

BACKGROUND

Moisture sensors for dew-point measurement are humidity-sensing capacitors. Currently most moisture sensors on the market use porous amorphous- or $\gamma$-$Al_2O_3$ films, formed by anodization in sulfuric acid solution. For simplicity, the amorphous/$\gamma$-$Al_2O_3$ films based moisture sensors are called $\gamma$-$Al_2O_3$ sensors. $\gamma$-$Al_2O_3$ sensors exhibit long-term drift of calibration curves. The mechanism for long-term drift of $\gamma$-$Al_2O_3$ sensors is caused by the phase change of $\gamma$-$Al_2O_3$, i.e. amorphous- or $\gamma$-$Al_2O_3$ changes to $\gamma$-$Al_2O_3 \cdot H_2O$ (boehmite) when it is exposed to moisture. This irreversible phase change causes volume expansion of aluminum oxide, resulting in gradual decrease in pore diameter and porosity so that its moisture adsorption capability is reduced. These $\gamma$-$Al_2O_3$ moisture sensors have to be calibrated constantly and also to be stored in a very dry environment. The accuracy and reliability of $\gamma$-$Al_2O_3$ moisture sensors are poor and it is also very inconvenient for users to use them. It is therefore very important to develop or invent a solid-state moisture sensor that is long-term stable and can be stored anywhere without special care.

In order to fabricate moisture sensors with high precision and long-term stability, $\gamma$-$Al_2O_3$ must be replaced or covered by a highly stable and moisture-sensing dielectric material. Toward this end, novel moisture sensor disclosed in this document use $SiO_2$ as a moisture sensing material. Actually $SiO_2$ is a unique material, which has been used in silicon-based integrated circuits for several decades. It is also sensitive to moisture because $SiO_2$ is hydrophilic. Therefore, $SiO_2$ can be used for moisture sensors if high-quality porous $SiO_2$ films can be obtained. However, it is very difficult to obtain high-quality porous $SiO_2$ films. The highest quality $SiO_2$ is formed by thermal oxidation of silicon. However, thermal $SiO_2$ can be grown only on silicon substrates, which cannot be used on other substrates. $SiO_2$ films can be deposited on other substrates by conventional deposition techniques, e.g., chemical vapor deposition (CVD), sputtering, and electron beam evaporation. However, it is well known that these $SiO_2$ films are non-stoicheometric with poor quality, low breakdown fields, and many defects. Furthermore, using the above methods one cannot deposit $SiO_2$ films conformally in high-aspect-ratio pores and therefore are not useful for moisture sensor fabrication. In recent years, a new deposition method, atomic layer deposition (ALD) emerged. ALD deposition of $SiO_2$ films can circumvent these problems because the material is deposited one atomic layer at a time, which can deposit thin $SiO_2$ films conformally on the inner surfaces of pores, and also controls the thin film thickness precisely at atomic scale.

SUMMARY

A novel moisture sensor comprises (a) a first electrode having a face, (b) a layer of porous insulated material having a first surface engaging that face, a second surface opposite the first surface and a plurality of pores, (c) a film of dielectric sensing material covering inner surfaces of the plurality of pores and the second face, and (d) a second electrode on the second face. In some embodiments at least a first group of the plurality of pores extends completely through the layer of porous insulating material from said first surface to the second surface. In some embodiments the film of dielectric sensing material covers the face of the first electrode within at least the first group of the plurality of pores. That first electrode may be made from a material selected from a group consisting of aluminum, titanium, gold, platinum, titanium nitride, silicon, and mixtures thereof. The layer of porous insulating material may be made from a material selected from a group consisting of alpha-phase alumina, gamma-phase alumina, amorphous alumina, silicon oxide, hafnium oxide, and mixtures thereof.

The film of dielectric sensing material may be made from a material selected from a group consisting of silicon dioxide, hafnium dioxide, and mixtures thereof. The second electrode may be made from a material selected from a group consisting of platinum, gold, titanium, titanium nitride and mixtures thereof.

In some embodiments the layer of porous insulating material has a thickness of between 10 nm and 50 μm and the film of dielectric sensing material has a thickness of between 0.5 nm and 500 nm.

In accordance with an additional aspect, a moisture sensor comprises (a) a substrate, (b) a first electrode having a first face, (c) a barrier layer having a second face engaging the first face and a third face opposite the second face, and (d) a layer of porous insulating material having a first surface engaging the third face, a second surface opposite the first surface and a plurality of pores. Further, the moisture sensor comprises (e) a film of dielectric sensing material covering inner surfaces of the plurality of pores in the second face and (f) a second electrode on said second surface. Still further, a method of manufacturing a moisture sensor comprises the steps of (a) forming a layer of porous insulating material on a face of a first electrode, (b) depositing a film of dielectric sensing material over the layer of porous insulating material including inner surfaces of a plurality of pores in the layer of porous insulating material and (c) depositing a second electrode over the film of dielectric sensing material. Further the method includes depositing the second electrode on an exposed surface of the film of dielectric sensing material outside of the plurality of pores so that the dielectric material deposited on the inner surfaces of the plurality of pores remains uncovered.

In the following description there is shown and described multiple embodiments of the moisture sensor. As it should be realized, the moisture sensor is capable of still other, different embodiments and its several details are capable of modification in various, obvious aspects. Accordingly, the drawings and descriptions should be regarded as illustrative in nature and not as restrictive.

BRIEF DESCRIPTION OF THE DRAWINGS

The accompanying drawings incorporated herein and forming a part of the specification, illustrate several aspects of the moisture sensor and together with the description serve to explain certain principles of the device. In the drawings.

Reference will now be made in detail to the three different embodiments of the moisture sensor illustrated in the accompanying drawings.

DETAILED DESCRIPTION

Figure 1:
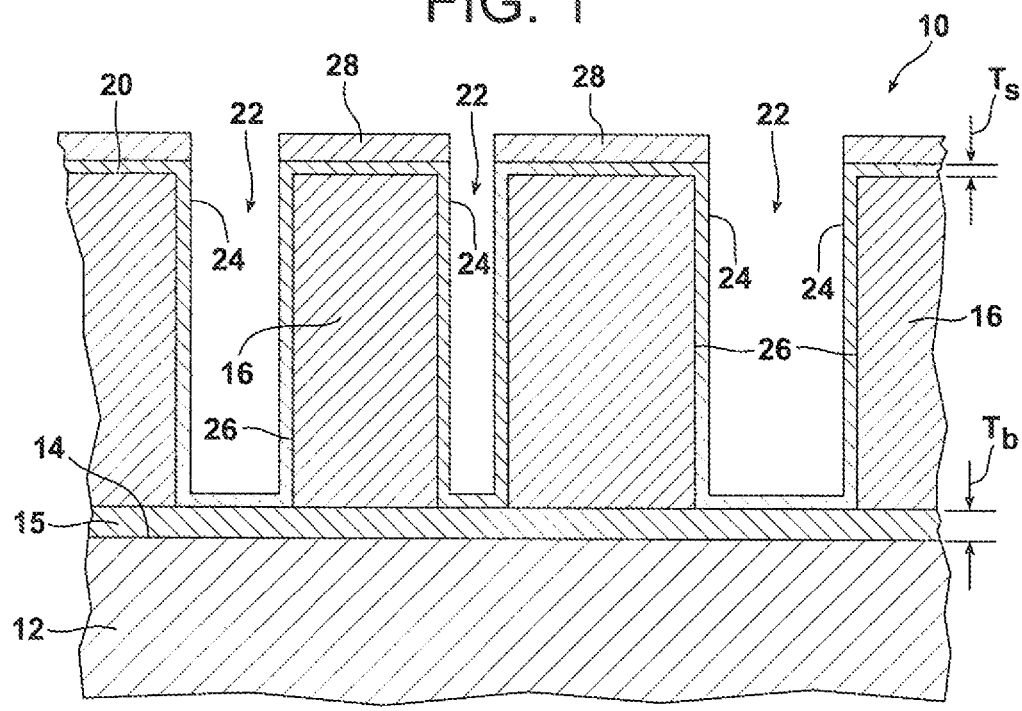
FIG. 1 is a schematic side elevational view of a first embodiment of a moisture sensor.
Figure 2:
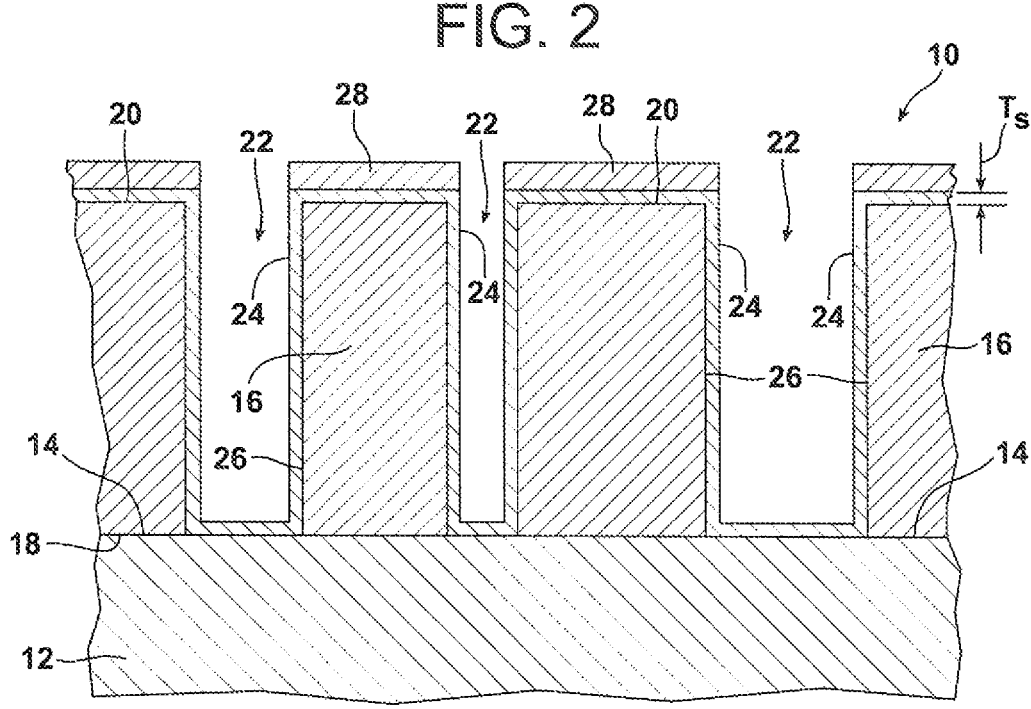
FIG. 2 is a schematic side elevational view of a second embodiment of the moisture sensor.

Reference is now made to FIGS. 1 and 2 illustrating two possible embodiments of a new and improved moisture sensor 10. The moisture sensor 10 includes a first electrode or conductive substrate 12 having a face 14. The first electrode may be made from a material including but not necessarily limited to, aluminum, titanium, titanium nitride, silicon and mixtures thereof. A barrier layer 15 covers the face 14. A layer of porous insulating material 16 has a first surface 18 engaging and covering the barrier layer 15 and a second surface 20 opposite the first surface. As should be appreciated, the porous insulating material includes a plurality of pores 22. The pores may range in diameter from about 5 nm to about 10 μm. Typically, the porous insulating material has a porosity of between about 10% and about 80%. The porous insulating material 16 may be made from a material including, but not necessarily limited to alpha-phase alumina, gamma-phase alumina, amorphous alumina, silicon oxide, hafnium oxide and mixtures thereof. The barrier layer 15 may be made, for example, from a material selected from a group consisting of gamma-phase alumina, amorphous alumina, silicon oxide, hafnium oxide, and mixtures thereof.

A film of dielectric sensing material 24 covers inner surfaces 26 of the plurality of pores 22 as well as the second face 20 of the porous insulating material 16. The film of dielectric sensing material 24 may be made from a material including, but not limited to, silicon dioxide, hafnium dioxide, and mixtures thereof.

As further illustrated in FIG. 1, a second electrode 28 is provided on and covers the second surface 20 of the porous insulating material 16. The second electrode is made from a material including, but not necessarily limited to, platinum, gold, titanium, titanium nitride and mixtures thereof. It should be noted that the second electrode 28 could be extended to partially cover the dielectric sensing material 24 on the side wall of pores 22 near the openings because there is no way to completely block the molecules from entering into the pores during deposition processes.

In the embodiment illustrated in FIG. 1, the plurality of pores 22 are closed at the bottom by the barrier layer 15 and do not extend completely through the porous insulating material 16 to the first electrode 12. In another possible embodiment illustrated in FIG. 2, there is no barrier layer. Thus, at least a first group of the pores 22 extends completely through the porous insulating material 16 from the first surface 18 to the second surface 20 so that the pores are open to the first electrode 12. In the second embodiment illustrated in FIG. 2, the film of dielectric material 24 covers the face of the first electrode 12 within at least the first group of the plurality of pores 22. In either of the embodiments the layer of porous insulating material 16 may have a thickness of between 10 nm and about 50 μm and the film of dielectric sensing material may have a thickness of between about 0.5 nm and about 500 nm.

Figure 3:
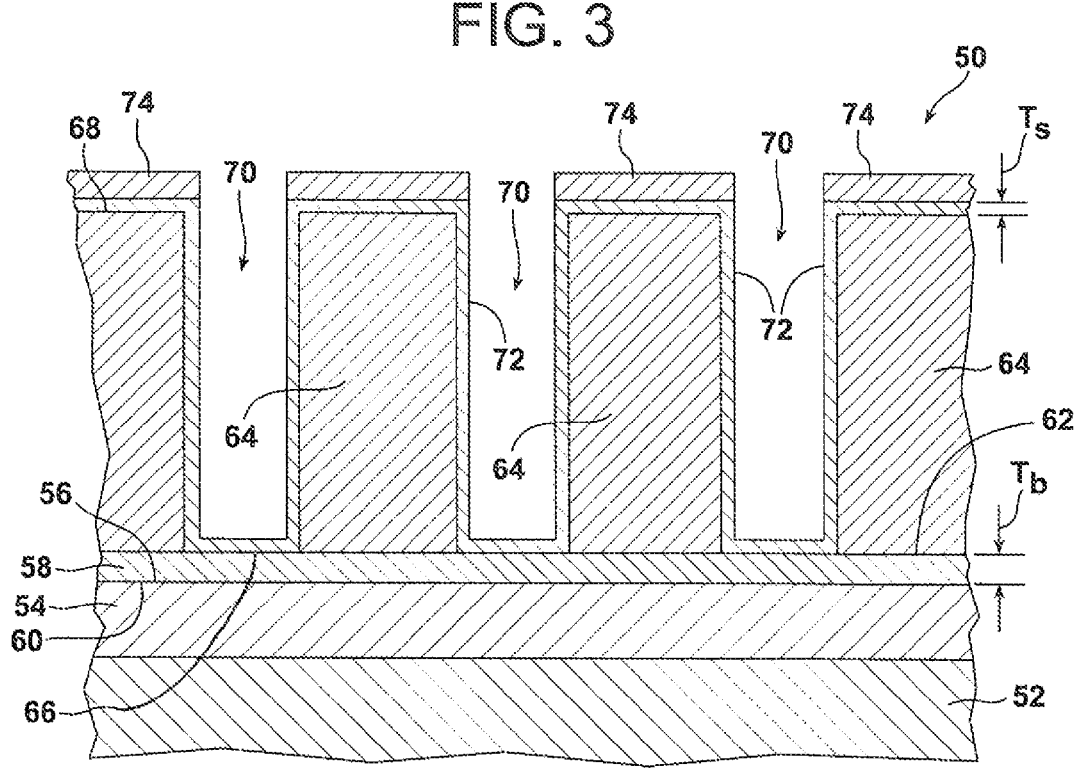
FIG. 3 is a schematic side elevational view of a third embodiment of the moisture sensor.

Yet another embodiment of moisture sensor 50 is illustrated in FIG. 3. The moisture sensor 50 includes a substrate 52 which may be made, for example, from a material selected from a group consisting of glass, quartz, oxidized silicon, silicon and mixtures thereof. A first electrode 54 is carried on the substrate 52. The first electrode may, for example, comprise a metal film such as, for example, a metal film constructed from a material consisting of aluminum, titanium, gold, platinum, titanium nitride and mixtures thereof.

The first electrode 54 includes a first face 56. A barrier layer 58 covers the first electrode 54. The barrier layer 58 has a second face 60 that engages the first face 56 and a third face 62 opposite the second face.

A layer of porous insulating material 64 has a first surface 66 engaging the third face 62, a second surface 68 opposite the first surface and a plurality of pores 70. The pores 70 may range in diameter from about 5 nm to about 10 μm.

A film of dielectric sensing material 72 covers the inner surfaces of the pores 70 and the second surface 68. As should further be appreciated the film of dielectric sensing material 72 also covers the exposed surface of the barrier layer 58 closing the bottom of the pores 70.

The moisture sensor 50 also includes a second electrode 74 engaging or covering the second surface 68 of the porous insulating material 64. It should be noted that the second electrode 74 could be extended to partially cover the dielectric sensing material 72 on the side wall of pores 70 near the openings because there is no way to completely block the molecules from entering into the pores during deposition processes.

Figure 4:
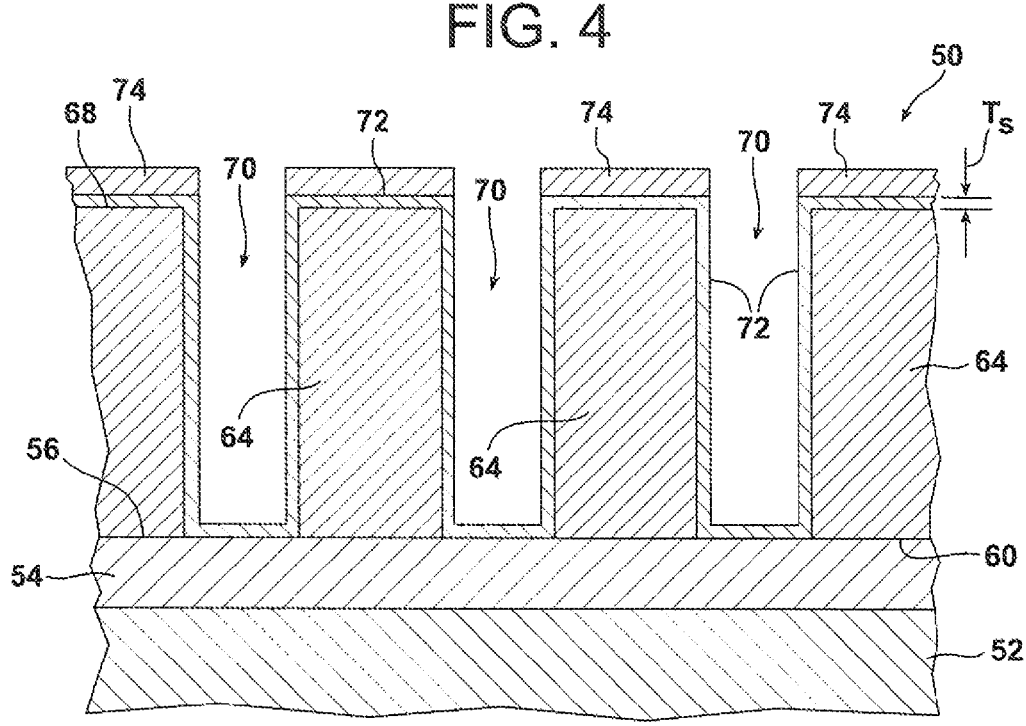
FIG. 4 is a schematic side elevational view of a fourth embodiment of the moisture sensor.

The first electrode 54, porous insulating material 64, film of dielectric sensing material 72 and second electrode 74 of this third embodiment of sensor 50 may be made, for example, from the same materials as used for those structures in the first two embodiments described above. The barrier layer 58 may be made, for example, from a material selected from a group consisting of gamma-phase alumina, amorphous alumina, silicon oxide, hafnium oxide, and mixtures thereof. FIG. 4 illustrates yet another embodiment which is very similar to the FIG. 3 embodiment but does not include a barrier layer. Thus, the pores 70 are open at the bottom to the first electrode 54.

A method of manufacturing a moisture sensor 10, 50 such as described above may be broadly described as comprising the steps of forming a layer of porous insulating material 16 on a face 14 of a first electrode 12, depositing a film of dielectric sensing material 24 over the layer of porous insulating material 16 including inner surfaces 26 of pores 22 in the layer of porous insulating material and depositing a second electrode 28 over the film of dielectric sensing material. In some embodiments the method includes the step of depositing the second electrode 28 on the exposed surfaces of the film of dielectric sensing material 24 outside of the plurality of pores 22 so that the dielectric sensing material deposited in the inner surfaces of the pores remains uncovered or exposed.

In accordance with yet another aspect, the method includes a step of depositing a film of silicon dioxide ($SiO_2$) by means of atomic layer deposition as the film of dielectric sensing material 24, 72 covering inner surfaces of the plurality of pores 22, 70. Advantageously, the atomic layer deposition process provides a relatively consistent layer of silicon dioxide dielectric sensing material over the inner surfaces of the pores including the bottom of the pores. This is an important factor in the enhanced sensitivity and long term stability of the moisture sensors 10, 50.

The following examples are presented to further illustrate how to make the moisture sensors 10, 50. The moisture sensors 10, 50 in these examples are based on silicon dioxide thin film as a sensing layer.

On a conductive substrate, a porous insulating material is formed. On the porous insulating material, thin $SiO_2$ film (0.5-500 nm thick) is then deposited on the inner surfaces of the pores. A thin metal film is deposited on the top surface of the porous structure, which serves as the top electrode. The conductive substrate serves as the bottom electrode.

The porous insulating material can be $\alpha$-$Al_2O_3$ formed by anodic spark deposition on an aluminum substrate, or amorphous/$\gamma$-$Al_2O_3$ formed by anodic oxidation of aluminum (AAO), or some other porous structures. An insulating barrier layer with a thickness of $T_b$ with variable values ($T_b$=0-300 nm) may exist at the pore base. For porous $\alpha$-$Al_2O_3$ films formed by anodic spark deposition, $T_b$ is near zero. For porous amorphous/$\gamma$-$Al_2O_3$ (AAO), there is a barrier layer at the pore base of pores. It may be reduced by etching the pore base. The $SiO_2$ thin film deposition method includes atomic layer deposition (ALD), chemical vapor deposition (CVD), and physical vapor deposition (sputtering). Conformal $SiO_2$ thin film deposited by atomic layer deposition (either thermal ALD or plasma ALD), is preferred. This is because $SiO_2$ thin film can be deposited using ALD on the inner surface of high-aspect ratio pores including the pore bases. The thin metal film, which serves as the top electrode, can be platinum, gold, titanium, titanium nitride, and their combination.

EXAMPLE 1 (FIG. 2)

Figure 5:
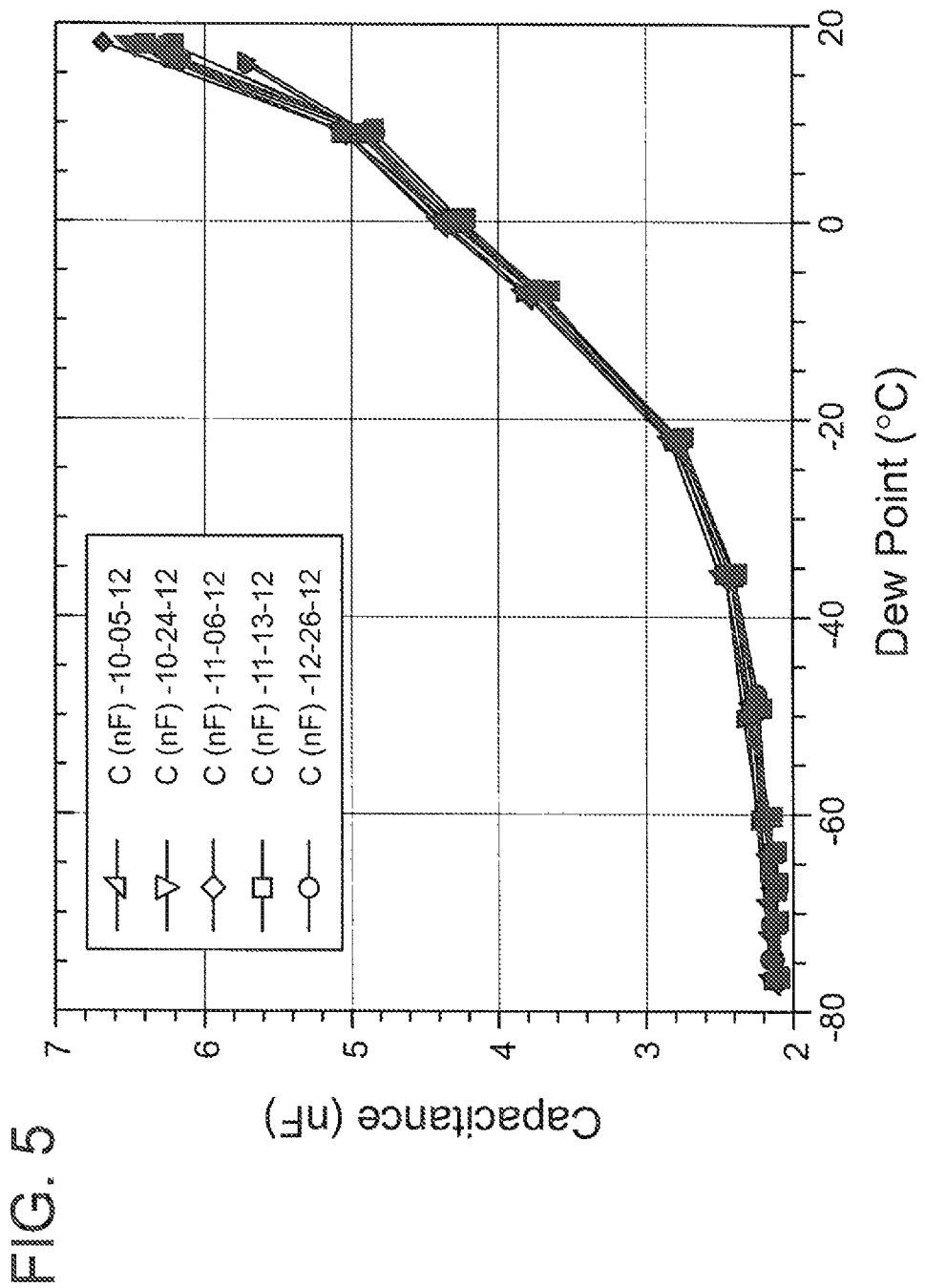
FIG. 5 is a graph plotting capacitance versus dew point for one possible embodiment for moisture sensor constructed in accordance with the teachings of this document.

Porous $\alpha$-$Al_2O_3$ based $SiO_2$ moisture sensors. The porous $\alpha$-$Al_2O_3$ based $SiO_2$ sensors work properly only if the previously patented sensor structure for top electrode connection is used [Zhi David Chen and Ibrahim Yucedag, U.S. patent application Ser. No. 13/416,437, the full disclosure of which is incorporated herein by reference]. An aluminum substrate with a rectangular shape was used. A small hole was drilled on the aluminum substrate, which would be used later for the bottom electrode connection. A dense $SiO_2$ layer of ~1-2 um was deposited using RF sputtering on one side of the aluminum substrate [U.S. patent application Ser. No. 13/416,437]. Then anodic spark deposition was carried out to form $\alpha$-$Al_2O_3$ on the part of the aluminum substrate that was not covered with the dense $SiO_2$ [U.S. patent application Ser. No. 13/416,437]. The details for porous $\alpha$-$Al_2O_3$ films formation by anodic spark deposition can be found in Z. Chen, M.-C. Jin, C. Zhen, and G. Chen, "Properties of Modified Anodic-Spark-Deposited Alumina Porous Ceramic Films as Humidity Sensors," *J. Am. Ceram. Soc.* 74, 1325 (1991); Z. Chen and M.-C. Jin, "An Alpha-Alumina Moisture Sensor for Relative and Absolute Humidity Measurement," in Proc. 27th Annual Conf. IEEE Industry Appl. Soc., IEEE Industry Appl. Soc., Houston, Tex., 1992, vol. 2, p. 1668. After anodic spark deposition, there were no barrier layers at the pore bases of porous $\alpha$-$Al_2O_3$ films, i.e. $T_b$=0. Then conformal $SiO_2$ thin films of ~2-10 nm were deposited on the surface, pore walls, and pore bases of porous $\alpha$-$Al_2O_3$ films by atomic layer deposition (ALD) using two step exposures: TDMAS precursor and ozone or three-step exposures: TDMAS, water, and ozone. Because $SiO_2$ growth was controlled at the atomic scale, very uniform and conform $SiO_2$ thin films was obtained. $SiO_2$ thin films deposited at the pore bases served as insulators. A metal film of 30-100 nm thick, e.g. platinum, gold, titanium, titanium nitride, and their combination, was deposited on the top of the porous structure, which served as the top electrode with the shape described in the U.S. patent application Ser. No. 13/416,437. The aluminum substrate served as the bottom electrode. The detailed wire connections can be found in the U.S. patent application Ser. No. 13/416, 437. It is well known that $\alpha$-$Al_2O_3$ (sapphire) is a highly stable phase. The entire sensor structure consisted of $\alpha$-$Al_2O_3$ and $SiO_2$, without amorphous/$\gamma$-$Al_2O_3$ at all, and was thus highly stable when interacting with water molecules. FIG. 5 shows the experimental test results of the porous $\alpha$-$Al_2O_3$-based $SiO_2$ moisture sensor at various moisture levels from −80° C. dew point to +20° C. dew point at room temperature 22° C. There was no drift at all for the two-and-half-months period of tests. In the intervals between the tests, the sensor was exposed to air in the lab at a natural humidity environment (10%-50% RH) without any protection. This suggests that this sensor has excellent long-term stability and high sensitivity and can be stored anywhere without special care.

EXAMPLE 2 (FIG. 3)

Porous amorphous/$\gamma$-$Al_2O_3$ based $SiO_2$ moisture sensors. An aluminum film is deposited on oxidized silicon substrates. The aluminum film is then photolithographically patterned in appropriate shapes as bottom electrodes. A porous amorphous/$\gamma$-$Al_2O_3$ film is formed on the aluminum film by anodic oxidation of aluminum as described in M. G. Kovac, D. Chleck, and P. Goodman, "A New Moisture Sensor for In-Situ Monitoring of Sealed Packages," *Solid State Technol.* 21, 35 (1978); M. G. Kovac et al., "Absolute humidity sensors and methods of manufacturing humidity sensors," U.S. Pat. No. 4,143,177 (1979); R. K. Nahar, "Physical Understanding of Moisture Induced Degradation of Nanoporous Aluminum Oxide Thin Films," *J. Vac. Sci. Technol.* B 20, 382 (2002); Z. Chen and C. Lu, "Humidity Sensors: A Review of Materials and Mechanisms," *Sensor Letters* 3, 274-295 (2005). An insulating barrier layer with a thickness of $T_b$ with variable values ($T_b$=0-300 nm) may exist at the pore base depending upon the pore base etching process. Then conformal $SiO_2$ thin films of ~2-20 nm are deposited on the surface, pore walls, and pore bases of porous $\gamma$-$Al_2O_3$ films by thermal atomic layer deposition using two step exposures: TDMAS precursor and ozone, or three-step exposures: TDMAS, water, and ozone; or plasma atomic layer deposition. Because $SiO_2$ growth is controlled at the atomic scale, very uniform and conform $SiO_2$ thin films can be obtained. A metal film of 30-100 nm thick, e.g. platinum, gold, titanium, titanium nitride, and their combination, is deposited on the top of the porous structure, which serves as the top electrode. The aluminum film serves as the bottom electrode. In this sensor structure, the amorphously-$Al_2O_3$ film is covered by a $SiO_2$ film, which may protect amorphous/$\gamma$-$Al_2O_3$ from interacting with water molecules. This protection is dependent on the thickness of $SiO_2$ films. The amorphous/$\gamma$-$Al_2O_3$-based $SiO_2$ sensors with a $SiO_2$ film of <5 nm thick may drift slightly in the initial several weeks because some water molecules may diffuse through the thin $SiO_2$ film, causing amorphous/$\gamma$-$Al_2O_3$ films degradation. After that, the sensors may become stable because of protection of the $SiO_2$ film.

In summary, numerous benefits result from employing the moisture sensors 10, 50 described in this document. Currently most solid-state moisture sensors on the market use porous amorphous- or $\gamma$-$Al_2O_3$ films, formed by anodization in sulfuric acid solution. These $\gamma$-$Al_2O_3$ moisture sensors exhibit long-term drift of calibration curves. Even the commercial aluminum oxide moisture sensors have to be calibrated twice a year to assure their accuracy and also to be stored in a very dry environment. It is very inconvenient for users. Because of high sensitivity and long-term stability, the novel $\alpha$-$Al_2O_3$- based SiO$_2$ moisture sensors 10, 50 described in this document will have great commercial potential to replace the current γ-Al$_2$O$_3$ moisture sensors on the market.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A moisture sensor comprising:
   a first electrode having a face;
   a layer of porous insulating material having a first surface engaging said face, a second surface opposite said first surface and a plurality of pores;
   a film of dielectric sensing material covering and contacting inner surfaces of said plurality of pores and said second surface, wherein the film defines an open space within the inner surfaces of the pores; and
   a second electrode opposite the dielectric sensing material and the porous insulating material from the first electrode.

2. A moisture sensor, comprising:
   a substrate;
   a first electrode carried on said substrate, said first electrode having a first face;
   a barrier layer having a second face engaging said first face and a third face opposite said second face;
   a layer of porous insulating material having a first surface engaging said third face, a second surface opposite said first surface and a plurality of pores;
   a film of dielectric sensing material covering and contacting inner surfaces of said plurality of pores and said second surface, wherein the film defines an open space within the inner surfaces of the pores; and
   a second electrode opposite the dielectric sensing material and the porous insulating material from the first electrode.

3. The sensor of claim 1, wherein said film of dielectric sensing material covers said face of said first electrode within at least said first group of said plurality of pores.

4. The sensor of claim 1, wherein at least a first group of said plurality of pores extends completely through said layer of porous insulating material from said first surface to said second surface.

5. The sensor of claim 1, wherein said first electrode is made from a material selected from a group consisting of aluminum, titanium, gold, platinum, titanium nitride, silicon and mixtures thereof.

6. The sensor of claim 1, wherein said layer of porous insulating material is made from a material selected from a group consisting of alpha-phase alumina, gamma-phase alumina, amorphous alumina, silicon oxide, hafnium oxide, and mixtures thereof.

7. The sensor of claim 1, wherein said film of dielectric sensing material is made from a material selected from a group consisting of silicon dioxide, hafnium dioxide, and mixtures thereof.

8. The sensor of claim 1, wherein said second electrode is made from a material selected from a group consisting of platinum, gold, titanium, titanium nitride and mixtures thereof.

9. The sensor of claim 1, wherein said layer of porous insulating material has a thickness of between 10 nm and 50 μm and said film of dielectric sensing material has a thickness of between 0.5 nm and 500 nm.

10. A moisture sensor, comprising:
    a substrate;
    a first electrode carried on said substrate, said first electrode having a first face;
    a barrier layer having, a second thee engaging said first face and a third face opposite said second face;
    a layer of porous insulating material having a first surface engaging said third face, a second surface opposite said first surface and a plurality of pores;
    a film of dielectric sensing material covering and contacting inner surfaces of said plurality of pores and said second surface; and
    a second electrode opposite the dielectric sensing material and the porous insulating material from the first electrode.

11. The sensor of claim 10 wherein said first electrode is made from a material selected from a group consisting of aluminum, titanium, gold, platinum, titanium nitride and mixtures thereof.

12. The sensor of claim 10 wherein said layer of porous insulating material is made from a material selected from a group consisting of alpha-phase alumina, gamma-phase alumina, amorphous alumina and mixtures thereof.

13. The sensor of claim 10 wherein said film of dielectric sensing material is made from a material selected from a group consisting of silicon dioxide, hafnium dioxide, and mixtures thereof.

14. The sensor of claim 10 wherein said second electrode is made from a material selected from a group consisting of platinum, gold, titanium, titanium nitride and mixtures thereof.

15. The sensor of claim 10, wherein said barrier layer is made from a material selected from a group consisting of gamma-phase alumina, amorphous alumina, silicon oxide, hafnium oxide, and mixtures thereof.

16. The sensor of claim 10, wherein said layer of porous insulating material has a thickness of between 10 nm and 50 μm and said film of dielectric sensing material has a thickness of between 0.5 nm and 500 nm.

17. A method of manufacturing a moisture sensor comprising:
    forming a layer of porous insulating material of a face of a first electrode;
    depositing a film of dielectric sensing material on said layer of porous insulating material including contacting inner surfaces of a plurality of pores in said layer of porous insulating material, wherein the film defines an open space within the inner surfaces of the pores; and
    depositing a second electrode over said film of dielectric sensing material, with the porous insulating material and the dielectric sensing material positioned between the first electrode and the second electrode.

18. The method of claim 17 including depositing said second electrode on an exposed surface of said film of dielectric sensing material outside of said plurality of pores so that said dielectric sensing material deposited on said inner surfaces of said plurality of pores remains uncovered.

19. The method of claim 17 including depositing a film of silicon dioxide by means of atomic layer deposition as said film of dielectric sensing material covering said inner surfaces of said plurality of pores.

20. The moisture sensor of claim 1 wherein said plurality of pores extend between said first surface and said second surface.

* * * * *